United States Patent [19]
Gopikanth

[11] Patent Number: 4,589,418
[45] Date of Patent: May 20, 1986

[54] COATING FOR SILVER/SILVER CHLORIDE REFERENCE ELECTRODE

[75] Inventor: Mysore L. Gopikanth, Burlington, Mass.

[73] Assignee: Cardiac Pacemakers, Inc., St. Paul, Minn.

[21] Appl. No.: 642,056

[22] Filed: Aug. 17, 1984

Related U.S. Application Data

[63] Continuation of Ser. No. 447,436, Dec. 6, 1982, abandoned.

[51] Int. Cl.4 .............................................. A61B 5/00
[52] U.S. Cl. ............................. 128/635; 128/419 PG; 128/783
[58] Field of Search ................... 128/783–786, 128/635, 908, 419 R, 419 P, 419 PG; 204/403, 410, 415, 431, 433, 435

[56] References Cited
U.S. PATENT DOCUMENTS
4,409,980 10/1983 Yano et al. ........................ 128/635

Primary Examiner—Edward M. Coven
Attorney, Agent, or Firm—Orrin M. Haugen; Thomas J. Nikolai

[57] ABSTRACT

A film coating for use in combination with an in-vivo signal generating reference electrode coupled to a condition responsive means and adapted to sense a condition of a body fluid within the host, wherein the film coating comprises a silicone based polymer having adhesive and cohesive properties performing an adherent and coherent film coating upon the signal generating reference electrode, and wherein the film contains potassium chloride therewithin in a concentration range between 20 and 40 milligrams per gram of polymer solids. The cross sectional thickness of the cured film is sufficiently large so as to stabilize and improve the mechanical properties of the electrode components, but sufficiently limited so as to reduce any adverse effect upon cell response.

3 Claims, 5 Drawing Figures

COATING FOR SILVER/SILVER CHLORIDE REFERENCE ELECTRODE

This is a continuation of application Ser. No. 447,436, filed Dec. 6, 1982, now abandoned.

BACKGROUND OF THE INVENTION

The present invention relates generally to an improved reference electrode system for monitoring certain parameters of blood, and more particularly to an improved coating for a reference electrode which is stable over extended periods of use, and thus capable of providing utility for an implantable device for the long-term and substantially continuous monitoring of blood parameters. Reference electrodes have been found useful in a number of blood monitoring applications, particularly in connection with determination of certain blood constituents, including pH, $PCO_2$ and the like. In these applications reference electrodes may be utilized as condition responsive sensors to determine the presence of these certain constituents and particularly when continuous long term monitoring is either necessary or desirable. One application for the apparatus of the present invention is as a coated reference electrode for determining certain constituents of blood, and wherein the electrode is used in combination with an implantable cardiac pacer device. Such an arrangement utilizes the improved electrode for controlling one or more of the operating parameters of an implanted pacer while the pacer is being employed in connection with the long-term pacing of a patient's heart. In such an arrangement, operational parameters of the pacer will be determined in part by the condition responsive blood monitoring sensor of the present invention.

In the utilization of reference electrodes for blood monitoring applications, it is desirable, if not requisite, that the reference electrode be selected so as to be entirely passive to the tissue in the patients system. Adverse tissue reactions, such as inflammatory reactions and the like must be avoided, particularly when considering the utilization of the reference electrode for long term implantation applications. The coating of the present invention includes the utilization of a membrane having good electrical and mechanical properties while acting to physically separate the surface of the reference electrode from direct contact with the blood. This membrane must, of course, be sufficiently permeable to blood or at least to the constituents being measured so as to provide accurate, responsive, and reliable signals. Furthermore, the cross-sectional thickness of the film must be sufficiently limited so as to permit reasonable response times for the reference electrode, while being sufficient to provide surface isolation along with mechanical durability.

In connection with the present invention, the reference electrode is preferably silver/silver chloride, with such an electrode being desireable from the standpoint of reliability and stability within the hostile environment of the host body. However, silver chloride/silver when used alone has been found to be somewhat inflammatory toward human tissue. In accordance with the present invention, however, the silver chloride/silver reference electrodes are rendered essentially passive to tissue through encapsulation or coating of the reference electrode with the film prepared in accordance with the present invention. Also, the silver chloride portion of the reference electrode tends to be somewhat frangible, and the film coating of the present invention improves the durability and mechanical properties of the electrode. The coating material may find utility when used in combination with materials other than silver/silver chloride.

SUMMARY OF THE INVENTION

Briefly, in accordance with the present invention, the reference electrode, preferably silver/silver chloride, is coated with a thin film of a silicone base polymer having both adhesive and cohesive properties, with the film containing saturated potassium chloride in a concentration range of between about 20 milligrams and 40 milligrams of KCl per gram of silicone polymer solids. Normally, the thickness of the film is between about 3 and 8 mils, with film thicknesses of between about 3 mils and 6 mils being preferred. Silicone base polymers, of course, are suitably adapted for long term implantation applications, and have been approved in the past by the Food and Drug Administration for such application.

The utilization of potassium chloride in the silicone base polymer enhances the properties of the reference electrode and, being in physical contact with the reference electrode, contributes to the overall operation of the cell. Silver/silver chloride is preferred as a reference electrode since its potential is stable when employed as a half-cell in in-vivo applications.

The utilization of a silicone base polymer in accordance with the present invention increases tissue-electrode compatibility, and has been found to reduce, if not eliminate adverse tissue reactions, such as inflammation, and furthermore has been found to reduce the incidence of tissue fibrosis. The utilization of the film coating of the present invention also significantly reduces electro catalytic activity of the reference electrode while it is retained within the host body.

Therefore, it is a primary object of the present invention to provide an improved tissue compatible film coating for use in combination with a reference electrode for in-vivo sensing applications, including use as a long-term blood monitor within a host body.

It is yet a further object of the present invention to provide an improved film coating for use in combination with a reference electrode for in-vivo sensing of a condition within the host, and wherein the film coating is fabricated from a silicone base polymer containing crystalline potassium chloride therewithin.

Other and further objects of the present invention will become apparent from a study of the following specification, appended claims and accompanying drawing.

IN THE DRAWING

DESCRIPTION OF THE PREFERRED EMBODIMENT

Figure 1:
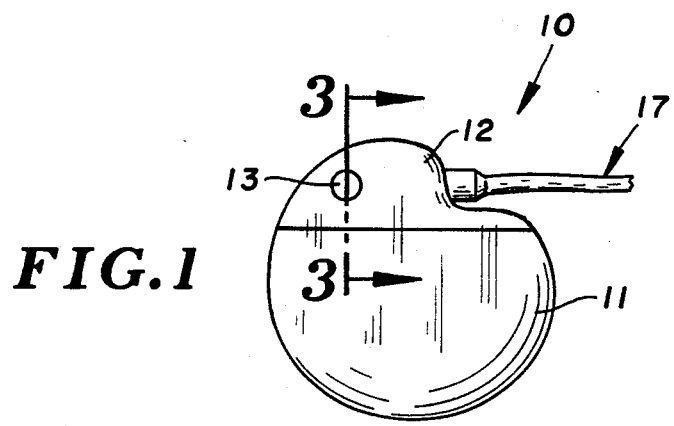
FIG. 1 is a side elevational view of a typical cardiac pacer device incorporating a silver/silver chloride reference electrode on one surface thereof and wherein the reference electrode is provided with a film coating, all in accordance with the present invention.
Figure 3:
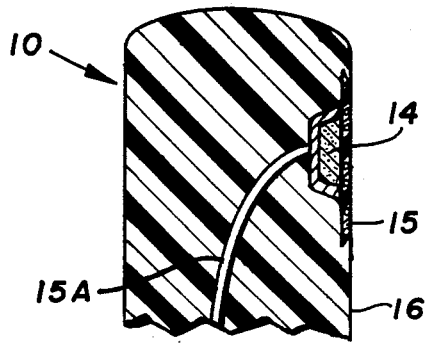
FIG. 3 is a sectional view taken along the line and in the direction of the arrows 3—3 of FIG. 1.

In accordance with the preferred embodiment of the present invention, and with particular attention being directed to FIGS. 1 and 3 of the drawing, the implantable cardiac pacer device generally designated 10 includes an hermetrically sealed pulse generator container 11 along with a lead receptacle portion 12 incorporated thereon. Shown mounted upon the surface of the lead receptacle 12 of the pacer 10 is a reference electrode assembly 13 which, as indicated, is in the form of a silver/silver chloride half cell. Typically, the reference electrode is formed by pressing a silver chloride pellet such as shown at 14 (FIG. 3) onto a silver substrate, with the electrode assembly thereafter being disposed along the surface of the pacer, preferably along the electrically insulative lead receptacle portion. Also, as will be apparent, the silver/silver chloride reference electrode is electrically coupled to the circuitry of the pacer through conductive lead 15A, the electrode assembly 13 being a signal generator responsive to the quantitative characteristics of certain blood constituents. The film coating 15 is generally in the range from about 3 mils to 10 mils, and preferably is about 3 mils in thickness. The film coating is a silicone base polymer suitable for long term implantation. Such silicone base polymers are, of course, commercially available, with one such polymer being available commercially under the designation "Silicone Type A" from Dow Corning Corp. of Midland, Mich., under the code name "Silastic Medical Adhesive" with preparation details for the film to be ultimately formulated being provided hereinafter.

Figure 2:
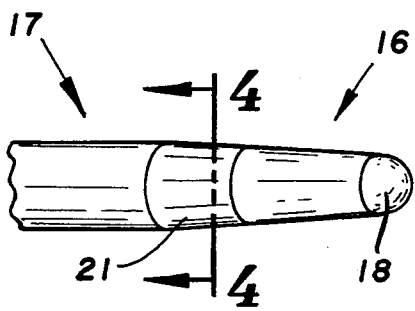
FIG. 2 is a perspective view of the electrode portion of a cardiac pacer lead, when wherein a reference electrode is secured to and mounted upon the tip portion of the lead for blood monitoring application.
Figure 4:
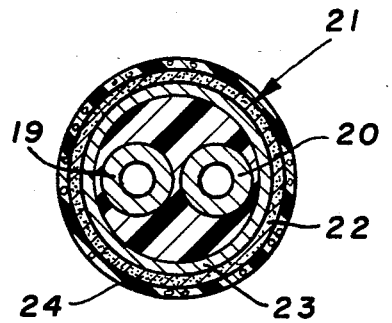
FIG. 4 is a sectional view taken diametrically through the leads of FIG. 2, and along the line and in the direction of the arrows 4—4 of FIG. 2.

With attention being directed to FIGS. 2 and 4, an alternate embodiment for the arrangement of the present invention is shown with this embodiment, utilizing a somewhat different form of reference electrode. In the embodiment of FIG. 2, the lead generally designated 17 is adapted to be electrically and mechanically coupled to the pulse generating circuitry of an implantable pacer through a lead receptacle 12 of the pacer of FIG. 1, with the reference electrode of the present invention, being alternatively situated along the surface of the lead. In the arrangement of FIG. 2, a typical cardiac stimulating and sensing electrode is shown generally at 16, with electrode 18 being disposed at the distal tip of the lead. Stimulating and sensing electrode 18 may be referred to as the active electrode. A insulative coating, typically a silicone based polymer, isolates the internal conductors, as illustrated at 19 and 20 from the body of the host. These internal conductors are utilized to couple the active electrode and the reference electrode to the pertinent components of the pulse generating circuitry. Such insulative coverings and internal conductors are, of course, well known in the art. Pacer leads having electrodes such as shown at 18 are in common use today, and with the exception of being provided with the reference electrode of the present invention, are commercially available. In the present instance, and as illustrated in FIG. 2, a reference electrode, such as reference electrode 21 is added to the lead configuration. The reference electrode 21 is a silver/silver chloride electrode shown in the configuration of an annular ring surrounding the lead assembly. Typically, the annular ring may be fabricated utilizing a substrate ring consisting of silver metal with edge flanges, and with a pellet of silver chloride being compressed as an annulus or annular ring into a cavity zone formed in the substrate ring. Depending upon the application, the silver chloride pellet may be in any convenient form, such as in the form of annular ring 22 as shown, and pressed into the silver substrate 23. This reference electrode is, in turn, coated with a film of silicone base polymer 24, containing crystalline potassium chloride therewithing. Alternatively, and in place of a closed and continuous ring, the pellet and substrate may comprise an arcuate segment only of an annular ring, such as an arcuate segment of about 90° or more.

In FIGS. 3 and 4, cross sections of the electrodes illustrated in FIGS. 1 and 2 respectively are illustrated, with each figure showing the physical arrangement of the silver metal substrate, the silver chloride pellet portion, and the film coating portion encapsulating the pellet and substrate.

Figure 5:
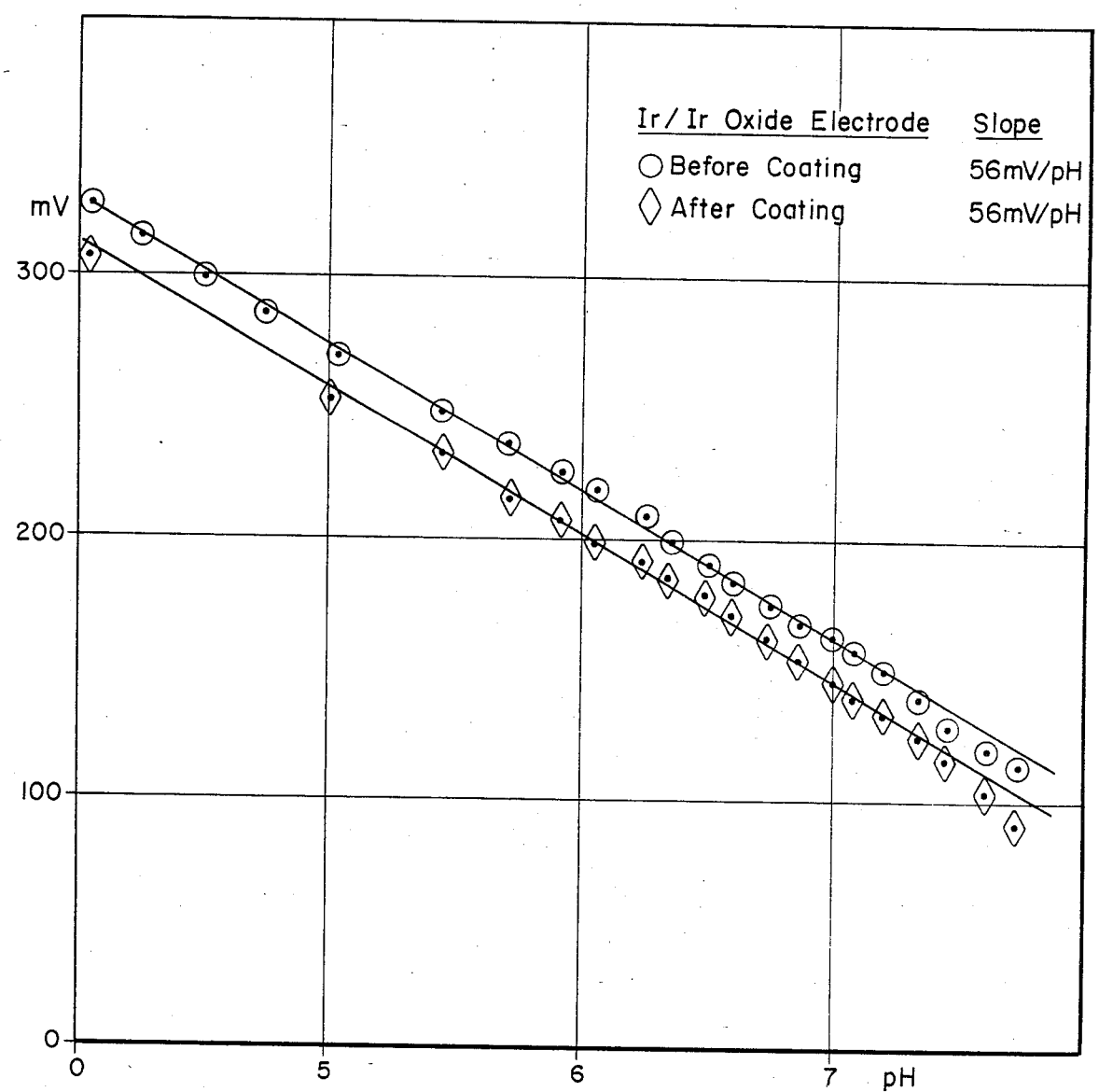
FIG. 5 is a graph of the electrical potentials obtained with the present invention.

Signal generating reference electrodes are desirable for use in long term blood monitoring applications. These signal generating reference electrodes are condition responsive, that is, provide a signal the amplitude of which varies in response to the condition being sensed. The signal generated by the reference electrode is, in turn, coupled to a signal pick-up means within the pulse generator portion of the pacer device. In this fashion, therefore, the reference electrode has the capability of sensing certain blood parameters, thereby determining certain conditions of the blood within the body of the host. In one application, the pH of blood may be determined by the reference electrode, with the silver/silver chloride cell providing an output signal with an amplitude indicitive of blood pH. With a film coating of a silicone polymer containing potassium chloride in a concentration of 30 milligrams per gram of silicone polymer solids, and with a film thickness of 5 mils, an electrical potential change of 56 mv/pH unit change was generated for pH variations in blood. It will be appreciated that changes in concentration of potassium chloride will result in corresponding changes in output level for the reference electrode, with such changes occurring under constant pH conditions. In the obtaining of data for FIG. 5, a silver/silver chloride pellet was utilized having a disc configuration, and being 5 mm in diameter, and 3 mm thick, and being held as a compress within a metallic silver substrate and exposed to blood. The electrical potentials obtained as shown in FIG. 5 were measured with reference to iridium/iridium oxide.

Cardiac pacer devices utilizing reference electrodes for determining blood pH have been known in the past. One such cardiac pacer device utilizing a reference electrode of silver/silver chloride is disclosed in Alcidi U.S. Pat. No. 4,009,721. However, the feature of the present invention permits long-term implantation of such a reference electrode without exposing the patient to problems of tissue irritation, inflammation, or the like.

FILM PREPARATION

In forming the active encapsulating or protective films of the present invention, Dow Corning Silastic Medical Adhesive Silicone Type A consisting essentially of a silicone base polymer was employed. In this application, Silastic, Medical Adhesive Silicone Type A (Dow Corning Medical Adhesive) silicone material was employed, with such materials being commercially available. A review of the chemistry, manufacture and uses of silicone polymers generally is given in "Encyclopedia of Polymer Science and Technology," Lichtenwalner et al, Volume 12 (Innerscience, New York, 1970) pp. 464–569.

In preparing the film, the silicone base polymer was thinned with a primer of 50:50 hexane/heptane by volume, with the polymer/primer mixture then being doped with potassium chloride crystals. Hexane/heptane primers are typically used with silicone polymers. After achieving an appropriate viscosity, the thinned-doped material was applied as a coating to the electrode. The potassium chloride present in the primer, remains in the polymer film, as shown in the drawing, and enhances the electrical properties of the cured film. The presence of potassium chloride in the polymer matrix provides for electrical conductivity in the film, and also provides for such conductivity without adverse reaction toward surrounding tissue.

I claim:

1. In combination; a pulse generator for a pacer adapted to periodically stimulate the heart tissue of a host and wherein the pulse generator comprises a power source with circuitry being coupled to the power source for generating periodic heart stimulation signals and with leads being coupled to the circuitry for delivering stimulation signals to the heart tissue, and a condition responsive electrical signal generating electrode adapted to be in direct contact with the blood of the host and responsive to the pH level of the blood of the host, and with said signal generating electrode being coupled to a signal pick-up means within the pulse generator portion of the combination, said combination being characterized in that:

(a) the signal generating electrode is a silver/silver chloride reference electrode having a condition responsive and active outer surface, a blood contacting film coating extending over said active outer surface and in direct surface-to-surface contact therewith; and (b) the film coating having a thickness of about 5 mils and being a silicone polymer containing potassium chloride solids dispersed within the silicone polymer film, said silicone polymer containing between about 20 and 40 milligrams of potassium chloride per gram of silicone polymer solids.

2. The combination of claim 1 being particularly characterized in that the potassium chloride is included at a level of about 30 milligrams of potassium chloride per gram of silicone polymer solids.

3. The combination as defined in claim 2 being particularly characterized in that said silicone polymer film has a thickness of about 5 mils.

* * * * *